(12) United States Patent
Landherr et al.

(10) Patent No.: US 8,267,885 B2
(45) Date of Patent: Sep. 18, 2012

(54) METHODS AND APPARATUS FOR DELIVERING PERITONEAL DIALYSIS (PD) SOLUTION WITH A PERISTALTIC PUMP

(75) Inventors: Frank J. Landherr, Cary, IL (US); Jay M. Lan, Thousand Oaks, CA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 560 days.

(21) Appl. No.: 12/347,663

(22) Filed: Dec. 31, 2008

(65) Prior Publication Data

US 2010/0168652 A1 Jul. 1, 2010

(51) Int. Cl.
*A61M 1/00* (2006.01)

(52) U.S. Cl. .......... 604/29; 604/151; 604/152; 604/153; 604/246; 604/260

(58) Field of Classification Search .............. 604/29, 604/151–153, 246, 260; 222/64, 255
See application file for complete search history.

(56) References Cited

U.S. PATENT DOCUMENTS

| | | | | |
|---|---|---|---|---|
| 3,713,743 A * | 1/1973 | Simms | ............. | 356/338 |
| 4,217,993 A * | 8/1980 | Jess et al. | ............. | 222/14 |
| 5,224,843 A | 7/1993 | van Lintel | | |
| 6,071,088 A * | 6/2000 | Bishop et al. | .......... | 417/322 |
| 6,743,201 B1 * | 6/2004 | Donig et al. | ............ | 604/114 |
| 6,758,975 B2 * | 7/2004 | Peabody et al. | ........... | 210/645 |
| 6,880,404 B2 | 4/2005 | Uberreiter | | |
| 7,104,768 B2 | 9/2006 | Richter et al. | | |
| 2005/0225201 A1 * | 10/2005 | Vogeley | .......... | 310/317 |
| 2006/0172954 A1 | 8/2006 | Jensen et al. | | |
| 2006/0186045 A1 | 8/2006 | Jensen et al. | | |
| 2007/0112603 A1 | 5/2007 | Kauthen et al. | | |
| 2008/0000835 A1 | 1/2008 | Rogers | | |
| 2008/0027374 A1 | 1/2008 | Jensen et al. | | |
| 2008/0045884 A1 | 2/2008 | Landherr et al. | | |
| 2008/0183126 A1 | 7/2008 | Landherr et al. | | |
| 2008/0183127 A1 | 7/2008 | Landherr et al. | | |
| 2009/0076856 A1 | 3/2009 | Darby et al. | | |
| 2009/0078592 A1 | 3/2009 | Jensen et al. | | |
| 2009/0264854 A1 | 10/2009 | Jensen et al. | | |

FOREIGN PATENT DOCUMENTS

WO WO-2007055136 A1 5/2007

* cited by examiner

*Primary Examiner* — Bhisma Mehta
*Assistant Examiner* — Larry R Wilson
(74) *Attorney, Agent, or Firm* — Nutter McClennen & Fish LLP; David J. Powsner; Andrew W. Schultz

(57) ABSTRACT

In one aspect, the invention provides methods and apparatus for delivering peritoneal dialysis (PD) solution (or other fluids), from a supply to a patient. A first pump, in fluid coupling with the supply, delivers PD solution from the supply to a "mesne" (or intermediate) measuring element, and generates signals indicative of a volume of that delivered PD solution. The mesne measuring element, in fluid coupling with the first pump, generates signals indicative of a volume of PD solution received from that pump. A second pump, fluidly coupled to the mesne measuring element, routes PD solution from the mesne measuring element for delivery to the patient.

21 Claims, 3 Drawing Sheets

METHODS AND APPARATUS FOR DELIVERING PERITONEAL DIALYSIS (PD) SOLUTION WITH A PERISTALTIC PUMP

BACKGROUND OF THE INVENTION

The invention relates to apparatus and methods for delivering fluids to a patient and, more particularly, to apparatus and methods for peritoneal dialysis (PD). It has application, inter alia, in the delivery of PD solution to a patient, for example, during automated peritoneal dialysis (APD) procedures.

Peritoneal dialysis (PD) is a medical procedure for removing toxins from the blood that takes advantage of the semipermeable membrane surrounding the walls of the abdomen or peritoneal cavity. During a PD procedure, a solution is introduced into the patient's abdomen, where it remains for up to several hours, removing blood toxins via osmotic transfer through that membrane. At completion of the procedure, the solution is drained from the body along with the toxins. In APD, the entire procedure is handled by automated equipment.

There are many systems on the market today for performing APD. Typically, such systems include a pumps and a variety of other complex components. In today's economy, cost is an ever-increasing issue, and PD equipment manufacturers have attempted to reduce production costs by several means. One is to employ peristaltic pumps, which can be inexpensive, though, they have inherent limitations. For example, accurately measuring the fluid volume delivered by a peristaltic pump can be difficult, e.g., because the tubing in the pump loses elasticity and, consequently, its volume changes over time. PD pumps also tend to develop pinhole leaks in pump tubing.

An object of the invention is to provide improved methods and apparatus for delivering fluid to a patient.

A further object of the invention is to provide such improved methods and apparatus for delivering PD solutions to a patient.

A still further object is to provide such improved methods and apparatus as can be adapted for using conventional pump technologies, e.g., peristaltic pumps.

A still further object of the invention is to provide such methods and apparatus as can be implemented at reasonable cost, yet, produce efficacious results.

SUMMARY OF THE INVENTION

In one aspect, the invention provides methods and apparatus for delivering peritoneal dialysis (PD) solution (or other fluids), from a supply to a patient. A first pump, in fluid coupling with the supply, delivers PD solution from the supply to a "mesne" (or intermediate) measuring element, and generates signals indicative of a volume of that delivered PD solution. The mesne measuring element, in fluid coupling with the first pump, generates signals indicative of a volume of PD solution received from that pump. A second pump, fluidly coupled to the mesne measuring element, routes PD solution from the mesne measuring element for delivery to the patient.

In related aspects, the invention provides methods and apparatus for delivering peritoneal dialysis (PD) solution as described above further comprising one or more digital data processors in communications coupling with any of the first pump and the mesne measuring element, wherein the one or more digital data processors provide for redundancy-based determination a volume of PD solution delivered to the patient in response to the signals generated by the first pump and/or the mesne measuring element.

In further related aspects, the invention provides methods and apparatus for delivering peritoneal dialysis (PD) solution as described above in which the second pump comprises a peristaltic pump. The peristaltic pump can route the PD solution directly to the patient or it may route it through an intermediary apparatus.

In still further related aspects, the invention provides methods and apparatus for delivering peritoneal dialysis (PD) solution as described above wherein the first pump includes a chamber in which the volume of delivered PD solution is determined, e.g., by one or more digital data processors responsive to signals generated by the first pump.

In other related aspects, the invention provides methods and apparatus for delivering peritoneal dialysis (PD) solution as described above in which the first pump comprises a piezoelectric ("piezo") pump. The piezo pump can, according to further related aspects of the invention, comprise a plurality of piezoelectric elements, e.g., piezo "strips," wherein at least one of those elements comprises a piezoelectric sensor, e.g., a piezo sensor strip. That strip can, according to related aspects of the invention, generate the volume-indicative signals discussed above.

The invention provides, in other related aspects, methods and apparatus for delivering peritoneal dialysis (PD) solution as described above in which signals generated by the first pump, e.g., the piezo pump, are proportional to the volume of delivered PD solution. In further related aspects, those signals are proportional to a volume of PD solution in the aforesaid chamber.

In related aspects, the invention provides methods and apparatus for delivering peritoneal dialysis (PD) solution as described above in which the first pump comprises a plurality of pumps, e.g., piezo pumps, each in fluid coupling with the supply, that deliver PD solution from it to the mesne measuring element. As above, one or more of those pumps can generate signals indicative of a volume of that delivered PD solution. These signals can represent, for example, time and/or voltage associated with activation of the piezo pumps.

In further related aspects, the invention provides methods and apparatus for delivering peritoneal dialysis (PD) solution as described above in which the first pump, e.g., the piezo pump (or pumps), generate(s) signals indicative of a volume of solution according to a duration of time empty the chamber (e.g., during the course delivering solution to the mesne measuring element).

In related aspects, the invention provides methods and apparatus for delivering peritoneal dialysis (PD) solution as described above in which the first pump delivers solution to the mesne measuring element at low-pressure and/or against a constant pressure head height.

In further related aspects, the invention provides methods and apparatus for delivering peritoneal dialysis (PD) solution as described above in which the mesne measuring element generates a volume-indicative signal (e.g., electrical, optical, etc.) based on a height of received PD solution in the chamber.

In related aspects, the invention provides methods and apparatus for delivering peritoneal dialysis (PD) solution as described above in which the mesne measuring element delivers the received PD solution to the second pump, e.g., via gravity-assist. In further related aspects, the invention provides methods and apparatus for delivering peritoneal dialysis (PD) solution as described above in which the second pump pulls the PD solution from the mesne measuring element for routing of the PD solution for delivery to the patient.

In related aspects, the invention provides methods and apparatus for delivering peritoneal dialysis (PD) solution as described above in which the first pump and the mesne measuring element are disposed within a removable and/or disposable cassette.

Further aspects of the invention are evident in the drawings and in the description that follows.

BRIEF DESCRIPTION OF THE DRAWINGS

A more complete understanding of the invention may be attained by reference to the drawings, in which.

DETAILED DESCRIPTION OF THE ILLUSTRATED EMBODIMENT

Figure 1A:
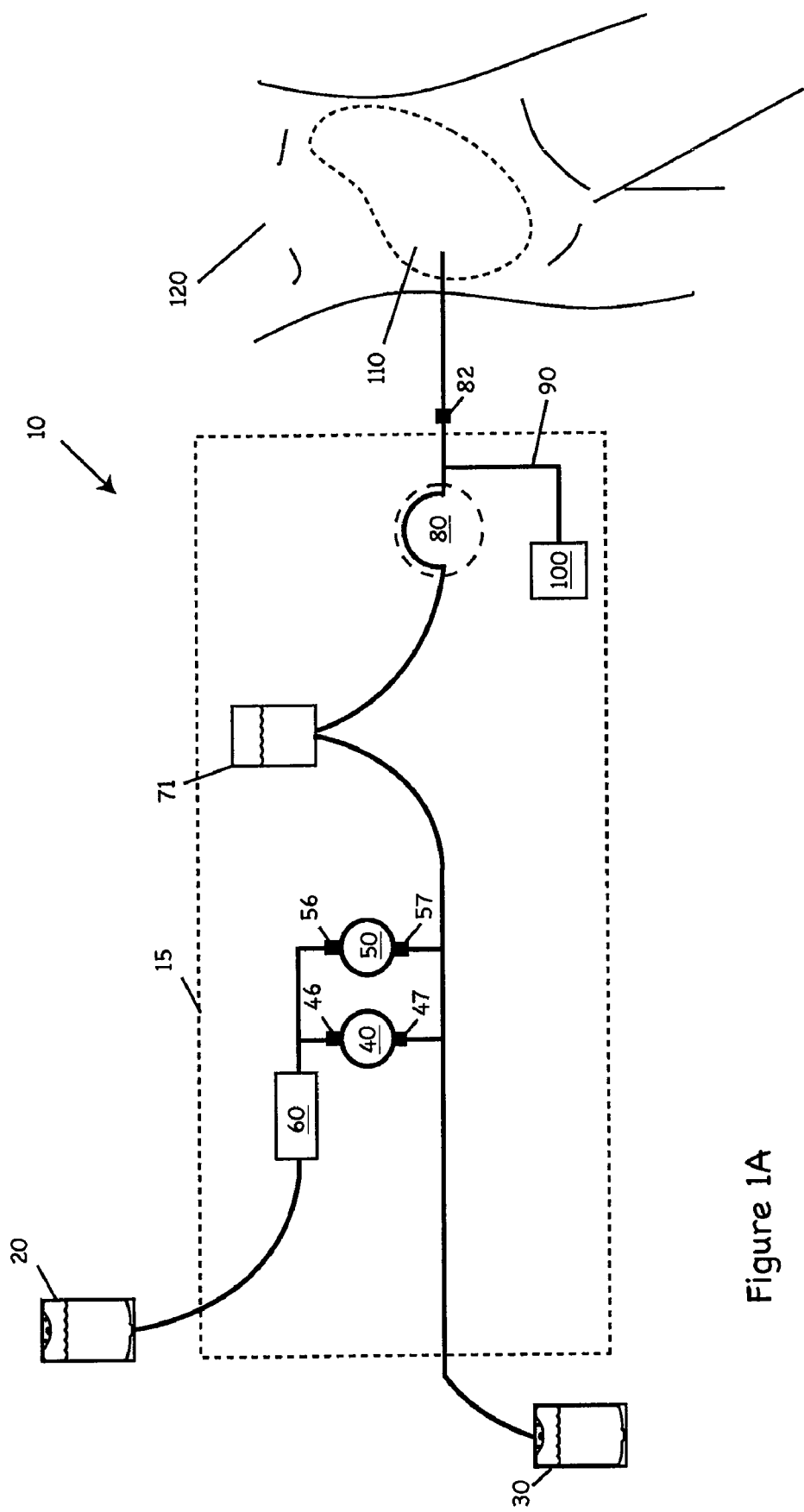
FIG. 1A depicts a system for delivering peritoneal dialysis (PD) solution from a supply to a patient according to one practice of the invention and of the type with which the invention can be practiced.

FIG. 1A depicts a peritoneal dialysis (PD) system 10 for delivering PD solution (or other fluid) to a patient according to one practice of the invention. The system 10 includes a supply bag 20 with fresh PD solution 25, a drainage bag 30, pumps 40 and 50, heater 60, solution chamber 71, pump 80, and pressure sensor 100. These elements are fluidly coupled (i.e., coupled for fluid flow) to one another, and with the patient, as indicated by the lines connecting them in the drawing and/or as discussed below. The system 10 facilitates inter alia introducing fresh PD solution into, and removing spent PD solution from, the peritoneum 110 of a patient 120.

In some embodiments, one or more components 40-100 are embodied within a removable cassette 15 which can be inserted into a suitably designed recess or receptacle of a dialysis machine or other apparatus (not shown) for delivering and/or routing PD solution (or other fluid) in accord with the teachings hereof. The cassette 15 comprises a base structure made of plastic, or other suitably rigid material, and can be constructed and operated as generally described, by way of non-limiting example, in commonly assigned U.S. Pat. No. 6,743,201, filed Apr. 1, 1999, entitled "Cassette for Delivering Fluids, Especially Dialysis Fluids" (the teachings of which are incorporated herein by reference), all as adapted in accord with the teachings hereof. Fluid coupling between the components 40-100 in these embodiments is provided by tubing or vias (ducts) intergral to and/or otherwise provided with the cassette 15, in the conventional manner known in the art as adapted in accord with the teachings hereof. Fluid coupling to the patient is provided via catheters and ports, and that with supply and drainage bags 20, 30 is provided via tubing—again, in the conventional manner known in the art.

In other embodiments, the components 40-100 may comprise functionality integral to and/or disposed within a dialysis machine (or other fluid delivery system) and/or they may comprise individual (or "stand-alone") elements which can be used, e.g., as part of a kit and/or within a variety of fluid delivery systems. As above, fluid coupling between the components in these embodiments is provided by tubing or vias (e.g., in the case of components integral to dialysis machines or other equipment), while coupling to the patient is provided via catheters and ports, and that with supply and drainage bags 20, 30, via tubing—all in the conventional manner known in the art as adapted in accord with the teachings hereof.

The supply bag 20 holds fresh PD solution 25 (or other fluid) for delivery to the patient 120 (or, more particularly, to the peritoneum 110, which detail will be assumed for the remainder of the discussion) and, in the illustrated embodiment, comprises a conventional PD solution supply bag of the type known in the art (e.g., a PVC plastic bag containing one to several liters of PD solution). The drainage bag 30 holds spent PD solution that has been drained from the peritoneum 110 of the patient 120 (e.g., via gravity-assist, pump 80 or otherwise), and, in the illustrated embodiment, comprises a conventional container of the type known in the art for this purpose (e.g., a PVC bag or otherwise).

The pumps 40 and 50 deliver PD solution (or other fluid) from the supply 20 to the solution chamber 71, a component of the mesne (i.e., "intermediate") measuring element 70 (see FIG. 2 and discussion below), and additionally facilitate measuring a volume of that delivered PD solution, as discussed further below. In the illustrated embodiment, the pumps 40 and 50 comprise piezoelectric pumps, though, in other embodiments they may comprise other types of pumps or apparatus for delivering and/or measuring fluids in accord with the teachings hereof. Although there are two pumps in the illustrated embodiment, other embodiments may include a greater or lesser number (piezoelectric or otherwise).

The heater 60 brings fresh PD solution to an appropriate temperature (e.g., 37° C.) for delivery to the patient 120. In the illustrated embodiment, the heater 60 comprises a heating element disposed in or around a fluid flow-line of cassette 15 that heats the PD solution as it passes from supply 20 to pumps 40 and 50. In other embodiments, the heater 60 is disposed in or around supply 20, pumps 40-50 and/or other elements of the illustrated system 10 upstream of patient 120. Examples of suitable heating elements include in-line heaters that provide thermo-acoustic heating, e.g., as maintained by processor or fuzzy logic 150 (hereinafter, "processor 150"). Indeed, in some embodiments, the cooling "side" of such heaters can be used to cool electronics and other components of the system 10, thereby, enabling a reduction in overall system size.

The solution chamber 71 holds and facilitates measuring a continuous flowing volume of PD solution (or other fluid) received from pumps 40 and 50 and passed to pump 80. The chamber 71 is sized for use with optical elements 72, 73 and, more generally, to afford measurement of continuous volumes or "batches" of the solution, e.g., in the manner discussed below. In the illustrated embodiment, the solution chamber 71 comprises a 40 mL chamber, though in other embodiments it may be sized otherwise, e.g., from 1-100 mL, 25-75 mL, or otherwise.

The chamber is preferably optically clear (or at least partially so) to wavelengths used to measure volumes of solution in it (again, as discussed below). For embodiments in which it forms part of a cassette 15, the chamber 71 comprises a cavity having walls of plastic (or other material) with apertures, fittings and/or otherwise shaped to accommodate elements 72, 73 and to allow light rays (e.g., visible, ultraviolet, infrared or otherwise) generated and received by them to pass with minimal attenuation therebetween. For cassette-less embodiments, element 71 can comprise a flow-chamber defined by like such walls integral to the fluid flow-path within a dialysis machine (or other fluid delivery system) and/or by a stand-alone vessel with suitable inlets and outlets. Although only one solution chamber 71 is shown in the drawing, other embodiments may include additional such chambers.

The pump 80 routes PD solution (or other fluid) received from the solution chamber 71 for delivery to the patient 120, either directly (e.g., via appropriate catheters and ports) or via additional apparatus (not shown) such as filtration equipment, additional heaters, monitoring apparatus, etc. In the illustrated embodiment, pump 80 comprises a peristaltic pump of the type known in the art, as adapted in accord with the teachings hereof, e.g., with flexible tubing or other structures suitable for defining an arc-like (or other) fluid-flow path that can be compressed by rollers (not shown), or the like, in a continuous rhythmic fashion to effect peristalsis—and, more particularly, to peristaltically pull fluid from chamber 71 and/or deliver it to patient 120 (again, directly or indirectly).

For embodiments utilizing a cassette 15, flexible tubing or other structures defining the compressible fluid-flow path of pump 80 can be embodied in and/or integral to the cassette, Moreover, the pump 80 can comprise an aperture and/or recess in cassette 15 adapted to receive one or more peristaltic pump rotors (with rollers) integral to the dialysis machine in which the cassette is inserted. For cassette-less embodiments, pump 80 can comprise a peristaltic pump defined by like tubing, rotors, etc., integral to a dialysis machine (or other fluid delivery system) and/or by a stand-alone vessel with suitable inlets and outlets. Although only one pump 80 is shown in the drawing, other embodiments may include additional such pumps (peristaltic or otherwise) instead of, or in addition to, the single pump 80 shown here.

The pressure sensor 100 facilitates measuring a pressure at which the pump 80 expels solution for delivery to the patient 120. The sensor comprises a conventional pressure sensor of the type known in the art and suitable for such purpose. In the illustrated embodiment, it is coupled to the output of the pump 80 via pressure line 90. The pressure sensor 100 generates an analog or digital output indicative of the sensed pressure for transmission to processor 150, which monitors (and logs) the pressure values to maintain, or otherwise manage, a pressure flow of the pump 80. In this regard, processor 150 can control the pump 80 speed in order to maintain the fluid pressure at the output of pump 80 within a predetermined range (e.g., between 1.0 and 2.0 pounds-per-square-inch or a pressure suitable neonatal solution delivery, etc.).

Figure 1B:
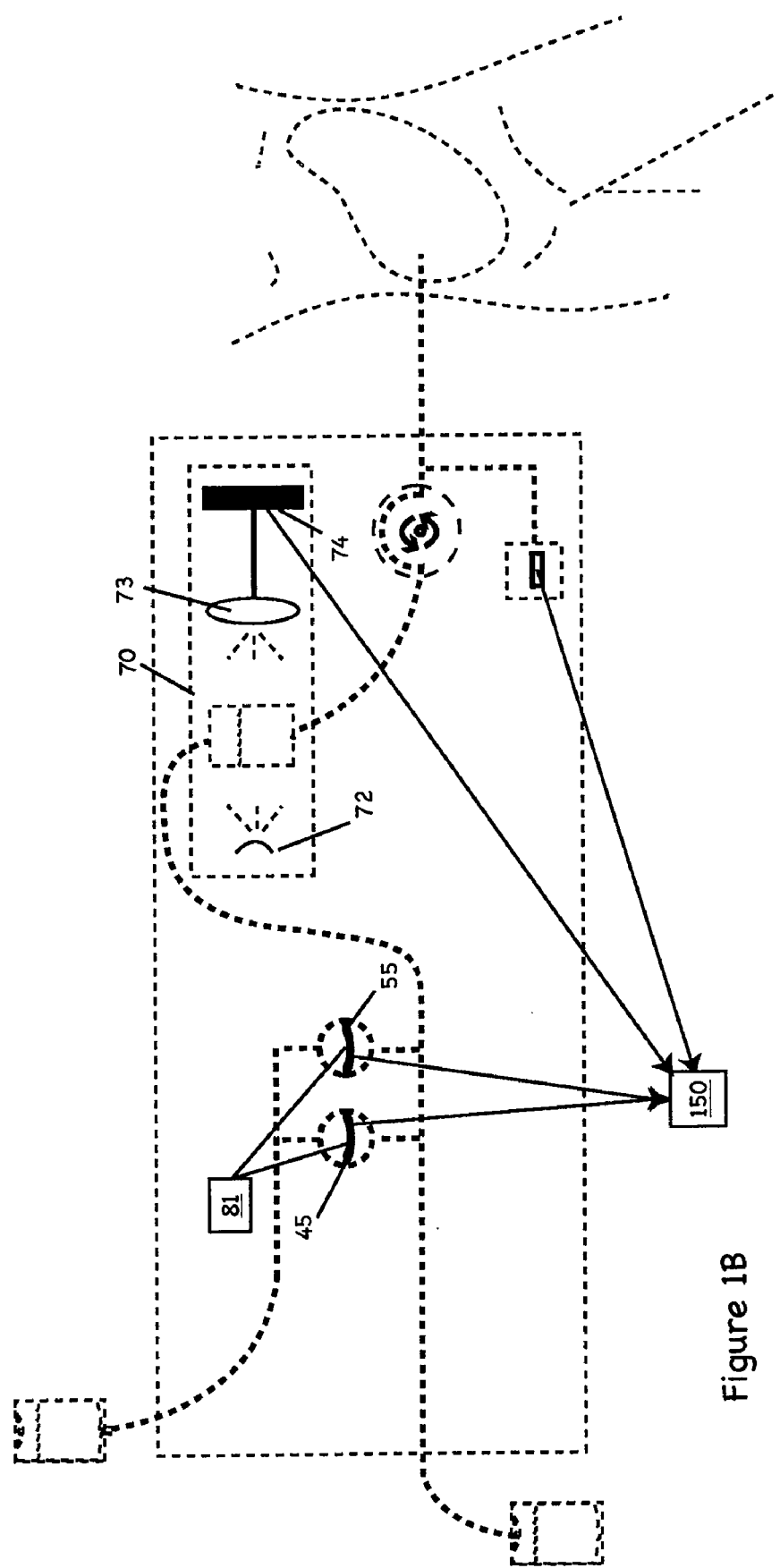
FIG. 1B depicts further details of the pumps and mesne measuring element of the system of claim 1.

FIG. 1B is a more detailed view of the PD system 10 of FIG. 1. The system 10 includes, inter alia, pumps 40 and 50, solution chamber 71 and pump 80, as discussed above. The text that follows further discusses these components and the remaining components of the mesne measuring element 70, namely, an illumination source 72, a lens system 73 and an image capture medium 74. Those skilled in the art will appreciate that other embodiments may include a greater or lesser number of such components, instead of, or in addition to, the components discussed below.

Generally, as discussed above, the pumps 40 and 50 deliver PD solution (or other fluid) from the supply 20 to the solution chamber 71 and additionally facilitate measuring a volume of that delivered PD solution. In the illustrated embodiment, the pumps 40 and 50 comprise piezo pumps that pump against a constant pressure head-height of the solution chamber 71 to effect delivery of the PD solution, although this is not a requirement of the system 10.

Figure 2:
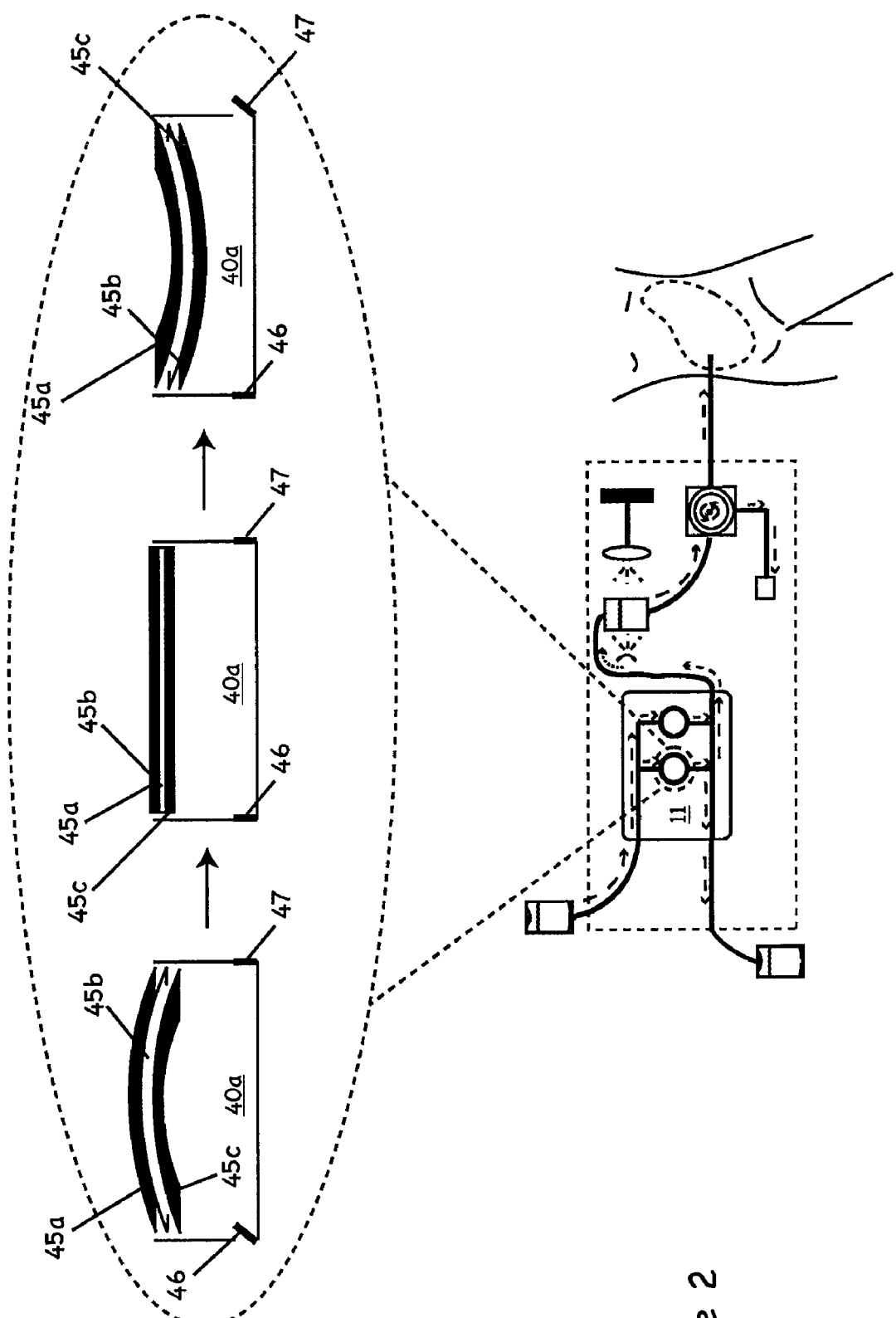
FIG. 2 depicts a more detailed view of bimorph-based pumps of the system illustrated in FIGS. 1A-1B.

Referring to FIG. 2, more particularly, pump 40 comprises a chamber 40a and a bimorph 45. In the illustrated embodiment, the bimorph 45 serves as a piston to draw PD solution (or other fluid) into and expel it from the pump chamber 40a (for routing to solution chamber 71). The chamber 40a is sized to accommodate the bimorph 45 and, in the illustrated embodiment, comprises a 20 mL chamber, though in other embodiments it may be sized otherwise, e.g., from 1 mL-100 mL, 25-75 mL, or otherwise.

The chamber 40a includes at least one inlet for receiving fluids, e.g., governed by valve 46, and at least one outlet for delivering fluids, e.g., governed by valve 47. For embodiments in which it forms part of a cassette 15, the chamber 40a comprises a cavity having at least one elastomeric or other flexible side-wall of latex, vinyl, and/or nitrile film (or other suitable material) against which bimorph 45 flexes and flattens, thereby, "pistoning" fluid into and out of the chamber 40a. In such an embodiment, the bimorph 45 is disposed outside the pump chamber 40a, in adhesive contact with the film. For cassette-less embodiments, element 40a can comprise a chamber having like flexible side wall(s) integral to a dialysis machine (or other fluid delivery system) and/or by a stand-alone vessel with such side wall(s). In these cassette-less embodiments, the bimorph 45 can be integral to the wall, e.g., without intervening elastomeric film.

In the illustrated embodiment, the bimorph 45 comprises a stack of one or more piezo strips or elements 45a-45c that alternatively flex and flatten, as driven by sinusoidally (or other) varying signals applied by a voltage source 81, thereby drawing fluid into and expelling it out of the chamber 40a. In this regard, action of the bimorph 45 is facilitated by valves 46, 47, positioned at the intake and exit of the chamber 40a, as illustrated, which can comprise piezoelectric valves driven (e.g., by voltage source 81 or otherwise) to open and close in synchronism with bimorph 45, although, in other embodiments they may comprise one-way mechanical valves, or the like. Such piezo valves can include feedback elements of the type described below that signal opening and closing of the valves, e.g., for use by processor 150 in controlling and/or logging system operation. Voltage source 81 of the illustrated embodiment is controlled by processor 150, e.g., to supply PD solution to chamber 71 at a rate coordinated with pump 80.

Illustrated bimorph 45 comprises three strips: two outer strips 45a, 45c that flex (in opposite directions) under an applied voltage, and one inner strip that generates an electrical signal (e.g., voltage or current) in response to flexing. The outer strips 45a, 45c are referred to as "actuator" strips. The inner strip 45b is referred to as a "sensor" or "feedback" strip. In the illustrated embodiment, each strip is sized sufficient to pump PD solution (or other fluid) at a low pressure (e.g., between 1.0 psi and 2.0 psi), and are sandwiched together via adhesive, ultrasonic welding, and so forth. Preferred materials for the strips 45 are polymers (e.g., polyvinylchloride and/or polyvinylflouride) or ceramics (e.g., lead zirconate titanate). Other embodiments may be constructed otherwise (e.g., fewer piezo strips, no feedback strip, additional feedback and/or sensing strips, varying materials, etc.).

As discussed above, the piezoelectric pump 40 also facilitates measuring a volume of PD solution in the chamber 40a. The illustrated feedback piezo strip 45b generates an electrical signal indicative of its degree and direction of bending, e.g., varying from a peak negative voltage or current when maximally flexed in one direction to a peak positive voltage or current when flexed maximally in the other direction. That electrical signal is transmitted to processor 150, which determines the volume of solution pumped in each cycle of element 40 as a function of the peak-to-peak timing and voltage.

More particularly, pump 40 and processor 150 are calibrated (e.g., at the manufacturing plant, upon insertion of cassette 15, at start of treatment or otherwise) by recording that peak-to-peak timing and voltage during movement of the bimorph 45 across an empty chamber 40a. Preferably, this is repeated several times in order to increase accuracy of the calibration. In operation, data processor 150 compares the calibration-phase peak-to-peak timings and voltages with those transmitted by the strip 45b while pumping PD fluid into and out of that same chamber 40a. The data processor then determines the volume of solution pumped in each cycle as a function of the difference in those timings and voltages, the volume of the chamber, the viscosity and specific gravity of the fluid. The processor also sums the per-cycle volumes to determined the overall volume delivered to chamber 71. The processor 150 monitors (and logs) values of those volumes to maintain, or otherwise manage, the pump 40—e.g., to control a rate which it supplies PD solution to chamber 71 and to control the amount of fluid delivered to it (and, ultimately, the patient).

Illustrated pump 50 (including, chamber 50a, bimorph 55, valves 56, 57) are constructed and operated similarly to pump 40 (and its constituent components), though, in other embodiments, pumps 40, 50 may be operated in other and/or dissimilar ways.

Referring back to FIG. 1B, the mesne measuring element 70 facilitates measuring a volume of PD solution (or other fluid) in the chamber 71. It includes, in addition to the chamber 71, an illumination source 72, lens system 73 and an image capture device 74. The illustrated illumination source 72 emits a pattern of light rays (e.g., visible, ultraviolet, infrared or otherwise) that are aimed to pass through the chamber 71, preferably, coherently (e.g., via laser "light"). Indeed, in some embodiments, the illumination source 72 generates these rays at two or more frequencies. Regardless, the wavelength(s) are selected for minimum attenuation in air and maximum attenuation in PD solution (or other delivered fluid). Accordingly, rays that pass through the filled, bottom region of the chamber are attenuated, while those that pass through the empty, top region are not. In the illustrated embodiment, the illumination source 72 comprises one or more laser diodes or laser diode arrays of the type commercially available in the marketplace, as adapted in accord with the teachings hereof. These can be arranged to emit a bar or grid pattern of rays that extends from the bottom to the top of the chamber 71. It will be appreciated that the rays emitted by source 72 may be formed into a pattern in other ways, as well, e.g., by etchings on walls of the chamber 71, and so forth.

The illustrated lens system 73 focuses and projects the rays that have passed through the chamber onto image capture device 74 to facilitate detection of a height (and, therefore, a volume) of solution in the chamber 71. Illustrated lens system 73 comprises one or more conventional lenses and/or prisms of the type commercially available in the marketplace suitable for such purpose, as adapted in accord with the teachings hereof.

Image capture device 74 captures the pattern of attenuated and unattenuated rays focussed thereon by the lens system 73. In the illustrated embodiment, the device 74 comprises a charge-coupled-device (CCD) array of 640×480 pixels, although in other embodiments it may comprise a smaller or larger array (e.g., a one-dimensional array, a lower-resolution array, etc.), and/or use different types of medium (e.g., CMOS sensors, etc). For higher resolution, larger arrays can be used. Typical pixel sizes for the arrays can range from 6.8 to 24 microns, though sizes on the smaller end of this range are preferable in order to improve accuracy. The illustrated CCD array 74 operates in the conventional manner known in the art of digital imaging, albeit as adapted in accord with the teachings hereof.

Processor 150 determines a volume of solution in the chamber 71 as a function of the pattern of rays captured by device 74. It does this periodically, e.g., over intervals that substantially the cycle time of pumps 40, 50. To this end, in the illustrated embodiment, by way of example, the processor 150 compares the captured pattern with one similarly generated during calibration phase—when the chamber 71 is empty. The comparison is performed using conventional image processing functions and the per-period volume determined as a function of the differences in the compared patterns. The processor 150 also sums the per-period volumes to determined the overall volume received at chamber 71. The processor 150 monitors (and logs) values of those volumes to maintain, or otherwise manage, coordinated operation of pumps 40/50 and 80, e.g., to control a rate which device 10 supplies PD solution to the patient.

Operation

In operation, by way of non-limiting example, the bags 20 and 30 are connected as shown in FIG. 1A-B, e.g., by a patient, medical assistant or otherwise. The solution is brought to temperature (e.g., 37° C.) by heater 60, and the processor 150 operates pumps 40, 50, drawing heated solution from the supply 20 to the chamber 71. Concurrently, the processor 150 determines a volume of that solution, all as described above.

Pump 80 delivers solution from chamber 71 to the patient (directly or indirectly), as described above, under control of processor 50. The volume of that solution is determined by the processor 150 based on the height of the solution in chamber 71 as detected by mesne measuring element 70, also as described above. The processor 150 compares the aforementioned volume determinations to determine—redundantly—how much solution has been delivered to the patient.

At conclusion of the treatment cycle, processor 150 opens a valve 82 downstream of pump 80 and simultaneously closes other valves (e.g., valves 46-49) to pump fluid expelled from the peritoneum 110 to drainage bag 30. In the illustrated embodiment, PD solution is drained via gravity-assist, although in other embodiments it may be pumped out (e.g., via pump 80 or otherwise).

Described and shown herein are apparatus and methods for delivering PD solution to a patient meeting the objectives set forth above. It will be appreciated that the embodiments described here are merely examples of the invention and that other embodiments, incorporating changes therein, fall within the scope of the invention. Thus, by way of non-limiting example, although the illustrated embodiment is directed to an apparatus for delivering PD solution to a patient, in other embodiments the invention may be utilized in the delivery of other solutions and fluids. And, by way of further non-limiting example, although cassette 15 may be replaced by multiple cassettes, each with a respective portion of the functionality of cassette 15.

In view thereof, what we claim is:

1. An apparatus for delivering peritoneal dialysis (PD) solution from a supply to a patient, comprising
    A. a piezoelectric ("piezo") pump that comprises a piezoelectric sensor, the piezo pump being in fluid coupling with a supply of PD solution and configured to pump PD solution from the supply to a mesne measuring element that includes a chamber, the piezo pump generating signals indicative of a volume of the PD solution pumped by it where those signals are indicative of a degree and direction of bending of the at least one piezoelectric sensor,
    B. the mesne measuring element, in fluid coupling with the first pump, generating signals indicative of a volume of PD solution within the chamber, and C. a second pump, fluidly coupled to the mesne measuring element, that routes PD solution from the mesne measuring element for delivery to the patient, wherein the second pump comprises a peristaltic pump, D. one or more processors in communications coupling with the piezo pump and the mesne measuring element, wherein the one or more processors determine a volume of PD solution delivered to the patient as a function of the volume-indicative signals generated by any of the piezo pump and the mesne measuring element.

2. The apparatus of claim 1, wherein the one or more processors compare the volume-indicative signals generated by the piezo pump and the mesne measuring element to determine, redundantly, how much PD solution has been delivered to the patient.

3. The apparatus of claim 1, wherein the piezoelectric sensor comprises at least one piezoelectric element that generates an electrical signal in response to flexing.

4. The apparatus of claim 1, wherein the signals generated by the piezo pump have peak-to-peak amplitudes and/or timings that are a function of the volume of PD solution pumped from the supply.

5. The apparatus of claim 1, comprising a plurality of said piezo pumps, each in fluid coupling with the supply, and each that pumps PD solution from the supply to the mesne measuring element, the plurality of piezo pumps each generating signals indicative of a volume of PD solution pumped by that respective pump.

6. The apparatus of claim 1, wherein the mesne measuring element generates the second volume-indicating signals based on a height of PD solution in the chamber of the mesne measuring element.

7. The apparatus of claim 6, wherein the mesne measuring element comprises one or more illuminant sources that transmit one or more rays of illuminant through the chamber of the mesne measuring element.

8. The apparatus of claim 7, wherein one or more of the rays transmitted by the illuminant source are coherent.

9. The apparatus of claim 7, wherein one or more of the rays transmitted by the illuminant source are generated by laser light emitting diodes.

10. The apparatus of claim 7, wherein the mesne measuring element comprises one or more image capture devices.

11. The apparatus of claim 10, wherein the mesne measuring element generates the volume-indicative signals as a function of a pattern of rays that are transmitted through the chamber of the mesne measuring element and that are captured by the one or more image capture devices.

12. The apparatus of claim 11, comprising a processor that compares the pattern of rays captured by the one or more image capture devices with one or more patterns generated during a calibration phase.

13. The apparatus of claim 11, comprising a processor that compares the pattern of rays captured by the one or more image capture devices with one or more patterns generated when the chamber of the mesne measuring element is empty of PD solution.

14. An apparatus for delivering peritoneal dialysis (PD) solution from a supply to a patient, comprising A. a plurality of piezoelectric ("piezo") pumps each of which comprises a chamber in fluid coupling with the supply and at least one piezoelectric sensor, the piezo pumps pumping PD solution in parallel from the supply to a mesne measuring element and generating first volume-indicating signals indicative of a volume of PD solution pumped by the piezo pumps to the mesne measuring element where those signals are indicative of a degree and direction of bending of the at least one piezoelectric sensor, B. the mesne measuring element including a chamber that receives PD solution from the piezo pumps, the mesne measuring element generating second volume-indicating signals indicative of a volume of the PD solution in the chamber of the mesne measuring element, and C. a peristaltic pump, fluidly coupled to the mesne measuring element, that routes PD solution from the mesne measuring element for delivery to the patient.

15. The apparatus of claim 14, wherein the peristaltic pump pulls the PD solution from the chamber of the mesne measuring element for delivery to the patient.

16. The apparatus of claim 14, wherein the peristaltic pump delivers the PD solution to the patient within a constant low-pressure range.

17. The apparatus of claim 16, wherein the low-pressure range is between 1.0 and 2.0 pounds-per-square-inch (psi).

18. The apparatus of claim 16 comprising one or more fuzzy logic and/or processing elements to monitor and/or control operation of the piezo pumps and the peristaltic pump.

19. The apparatus of claim 14, wherein at least one of
 i. the chamber of each of the plurality of piezo pumps is embodied in one or more cassettes,
 ii. the chamber of the mesne measuring element is embodied in said one or more cassettes,
 iii. the peristaltic pump comprises a fluid-flow path embodied in said one or more cassettes.

20. The apparatus of claim 14 comprising a pressure detection element, fluidly and/or electrically coupled to the peristaltic pump, that generates signals indicative of a pressure at which the peristaltic pump routes the PD solution for delivery to the patient.

21. The apparatus of claim 14, further comprising one or more processors in communications coupling with the piezo pump and the mesne measuring element that compare the volume-indicating signals generated thereby to determine, redundantly, a volume of PD solution delivered to the patient.

* * * * *